Figure 1:
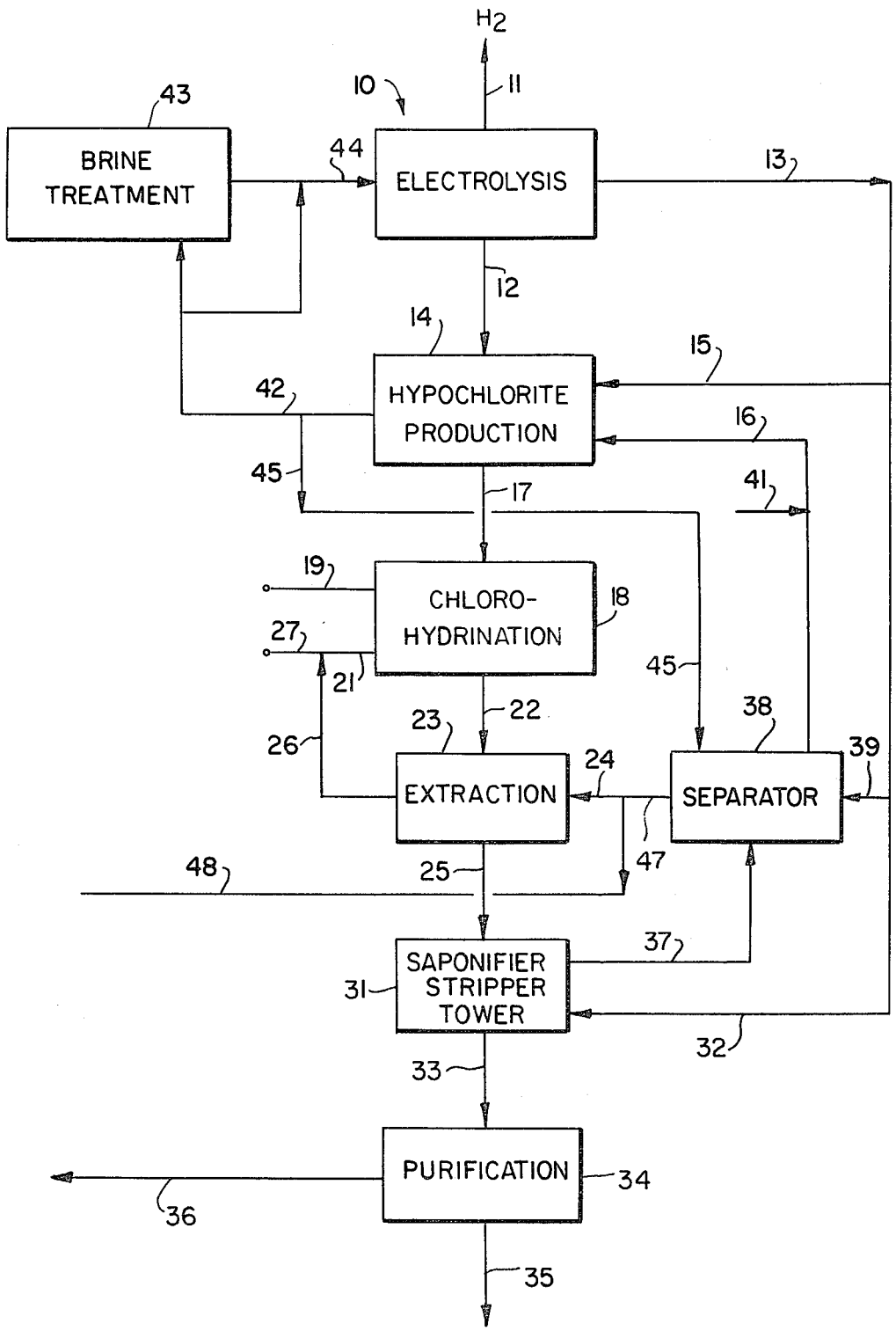

United States Patent [19]

Apanel

[11] 4,277,405

[45] Jul. 7, 1981

[54] PRODUCTION OF EPOXY COMPOUNDS FROM OLEFINIC COMPOUNDS

[75] Inventor: George J. Apanel, Bloomfield, N.J.

[73] Assignee: The Lummus Company, Bloomfield, N.J.

[21] Appl. No.: 35,560

[22] Filed: May 3, 1979

[51] Int. Cl.$^3$ .................... C07D 301/26; C25B 3/02; C25B 3/06
[52] U.S. Cl. .................... 260/348.21; 260/348.22; 204/79; 204/80; 204/81
[58] Field of Search .................... 260/348.21, 348.22, 260/348.18; 204/79, 80

[56] References Cited

U.S. PATENT DOCUMENTS 4,008,133  2/1977  Gelbein et al. ................. 260/348.18
4,126,526  11/1978  Kwon et al. .................... 260/348.21

FOREIGN PATENT DOCUMENTS 1291328  3/1969  Fed. Rep. of Germany ...... 260/348.21

Primary Examiner—Norma S. Milestone
Attorney, Agent, or Firm—Louis E. Marn; Elliot M. Olstein

[57] ABSTRACT

Olefin is reacted with alkyl hypochlorite and water to produce an effluent containing the chlorohydrin and alkanol. An organic solvent is employed to extract the alkanol and chlorohydrin from the aqueous effluent, followed by saponification with base to produce olefin oxide. Olefin oxide is separated from the saponification effluent, followed by separation of an organic phase of the organic solvent, and an aqueous phase, which contains the alkanol. The aqueous phase containing alkanol, is chlorinated to produce the alkyl hypochlorite, with the organic phase being recycled to the extraction. The process is preferably integrated with the electrolytic production of chlorine.

13 Claims, 2 Drawing Figures

PRODUCTION OF EPOXY COMPOUNDS FROM OLEFINIC COMPOUNDS

This invention relates to the production of epoxy compounds, and more particularly to new and improved process for producing epoxy compounds from olefinically unsaturated compounds via the chlorohydrin.

U.S. Pat. No. 4,008,133 describes a process for producing epoxy compounds from olefins, via the chlorohydrin, and is particularly related to a process for producing epoxy compounds which is integrated with an electrolytic process for producing chlorine, whereby the epoxy compound can be produced from olefin and water, as net starting materials. The present invention is directed to an improvement in a process for producing epoxy compounds from olefins, via the chlorohydrin.

In accordance with the present invention, there is provided an improvement in a process for producing an epoxy compound wherein a tertiary alkanol is chlorinated to produce tertiary alkyl hypochlorite, the tertiary alkyl hypochlorite is contacted with an olefinically unsaturated compound and water to produce a reaction effluent containing tertiary alkanol and chlorohydrin, and the chlorohydrin is saponified to produce the epoxy compound. In accordance with the improvement of the present invention, organics present in the chlorohydrin reaction effluent are recovered by use of an organic extraction solvent whereby the organic extraction solvent includes the chlorohydrin and tertiary alkanol. The organic extraction solvent, containing the chlorohydrin and tertiary alkanol is contacted with an aqueous base to effect saponification of the chlorohydrin to the corresponding epoxy compound. The epoxy compound is separated from the saponification effluent. Tertiary alkanol present in the saponification effluent is extracted into an aqueous phase which is employed in the hypochlorite production, and organic solvent is recycled to the chlorohydrin effluent extraction.

More particularly, tertiary alkanol is contacted with chlorine in the presence of aqueous caustic such as calcium hydroxide, potassium hydroxide, sodium hydroxide, etc., preferably sodium hydroxide, to convert the tertiary alkanol to tertiary alkyl hypochlorite. The tertiary alkyl hypochlorite is then reacted with olefinically unsaturated compound and water to produce the corresponding chlorohydrin and tertiary alkanol. Chlorohydrin and tertiary alkanol are extracted from the effluent by use of an organic solvent which may be present in the chlorohydrin production or added to the effluent. The organic extract is then contacted with a suitable aqueous base, such as sodium hydroxide, potassium hydroxide, calcium hydroxide, etc., preferably sodium hydroxide, to effect saponification of the chlorohydrin to the corresponding epoxy compound. The epoxy compound is recovered as product. Tertiary alkanol present in the saponification effluent is extracted into an aqueous phase for recycle to hypochlorite production. Organic solvent is recycled to the chlorohydrin effluent extraction.

The organic solvent employed in the process is inert, immiscible with the aqueous phases present in the process, and is a solvent for alkanol and chlorohydrin employed and/or produced in the process. The term "inert" as used herein means that the extraction solvent does not adversely affect the various reactions. As representative examples of suitable solvents, there may be mentioned: chlorinated hydrocarbons, including chlorinated aromatics and chlorinated aliphatics (saturated); e.g., chlorobenzene, chlorinated paraffins, such as carbon tetrachloride, chloroform, dichloropropane, polychlorinated paraffins, etc.; chlorinated ethers; e.g., bis(chloroisopropyl) ether, ketones and the like. Such solvents may be employed alone or as a mixture of two or more thereof. In accordance with a preferred aspect, the organic solvent has a boiling point less than the aqueous caustic solution employed for the saponification to facilitate recovery of the epoxy compound by steam stripping; i.e., reduction of reboiler temperature and lower steam consumption.

The aqueous alkali employed for the hypochlorite production and saponification may be the same or different alkali. Similarly, the alkali can be obtained from any one of a wide variety of sources. In accordance with a preferred procedure, the epoxy production is integrated with an electrolytic process for producing chlorine; however, the scope of the invention is not limited to such a preferred procedure. For example, chlorine can be obtained from other sources and/or alkali can be provided other than from the electrolytic cell.

In accordance with the preferred aspect of the present invention, gaseous chlorine is produced in an electrolytic cell by the electrolysis of an aqueous brine solution, with chlorine being produced at the anode and sodium hydroxide and hydrogen at the cathode. The gaseous chlorine produced in the electrolysis cell is reacted with a tertiary alkanol in an aqueous solution, containing sodium hydroxide and sodium chloride, obtained from the cathode compartment of the electrolytic cell to produce a tertiary alkyl hypochlorite. An organic phase, containing the tertiary alkyl hypochlorite, is recovered from the first reaction zone and contacted in a second reaction zone with an olefinically unsaturated compound and water to produce the corresponding chlorohydrin. An organic extraction solvent is employed to extract organics from the aqueous effluent, containing chlorohydrin and tertiary alkanol. The organic extract, including chlorohydrin and tertiary alkanol, is contacted with an aqueous solution of sodium hydroxide and sodium chloride, obtained from the cathode compartment of the electrolytic cell, to produce from the chlorohydrin the corresponding epoxy compound, which is recovered as reaction product. Epoxy compound is recovered as reaction product. Tertiary alkanol present in the effluent is extracted into an aqueous phase, which may be the aqueous phase present in the saponification effluent or an aqueous phase provided from the hypochlorite production, with the tertiary alkanol in the aqueous phase being recycled to the hypochlorite production. Organic solvent is recycled to the chlorohydrin effluent extraction.

In accordance with a preferred aspect, the electrolyte fed to the anode has a sodium chloride concentration from about 170 to about 400 grams per liter of water, and preferably from about 200 to about 350 grams per liter of water. In the electrolytic cell, chlorine is produced at the anode and hydrogen and sodium hydroxide are produced at the cathode.

Chlorine produced in the electrolytic cell is introduced into a hypochlorite production reaction zone wherein the chlorine is reacted with a tertiary alkanol, preferably a tertiary alkanol having from 4 to 6 carbon atoms, and most preferably tertiary butanol or tertiary amylalcohol, and sodium hydroxide in an aqueous brine solution, obtained from the electroytic cell.

In general, the hypochlorite production reactor is operated at a temperature from about 5° to 220° F., preferably at a temperature from about 32° to 160° F., a pressure from about 5 psia to 100 psia, preferably from about 10 psia to 50 psia.

In order to minimize the amount of free chlorine present in the alkyl hypochlorite organic phase introduced as feed to the chlorohydrin reactor, the hypochlorite production reaction can be effected without a substantial molar excess of chlorine with respect to sodium hydroxide. Accordingly, in order to minimize the quantity of free chlorine present in the hypochlorite reaction product, the molar ratio of chlorine to sodium hydroxide generally does not exceed about 1.05 to 1, and is preferably at about stoichiometric proportions; i.e., about 1:1.

In accordance with a preferred operation, the hypochlorite production reaction is effected in a manner such that the alkyl hypochlorite is formed as a separate organic phase to thereby eliminate the necessity of extracting the hypochlorite from the aqueous phase. In order to provide a separate organic phase, the hypochlorite production reaction is effected at a chlorine to sodium hydroxide mole ratio of at least 0.5:1. Thus, in accordance with the preferred operation, the hypochlorite production reaction is effected with chlorine to sodium hydroxide mole ratios of from about 0.5:1 to 1.05:1, and preferably from about 0.9:1 to 1:1.

In regard to the amount of tertiary alkanol employed with respect to the amount of sodium hydroxide, it is preferred to operate the hypochlorite production reactor without a substantial molar excess of sodium hydroxide with respect to the tertiary alkanol. In general, the mole ratio of tertiary alkanol to sodium hydroxide is from about 0.75:1 to about 1.1:1.

It is to be understood that the cell liquor could be partially chlorinated in a separate vessel by contact with a portion of the overall chlorine requirements to produce sodium hypochlorite, with the remainder of the chlorine requirements, the t-alkanol and partially chlorinated cell liquor being introduced into the hypochlorite production reaction. In such a two-step process, in general, less than about one-half of the total chlorine requirements are employed in the first stage to produce the sodium hypochlorite.

An aqueous brine phase and an organic phase, containing the hypochlorite, are separately recovered from the hypochlorite production reactor. The aqueous brine phase may then be introduced into the electrolytic cell, as electrolysis feed whereby the chlorine values are recovered therefrom.

The organic phase, recovered from the hypochlorite production reactor is then introduced into the chlorohydrin production reactor. In the chlorohydrin production reactor, the tertiary alkyl hypochlorite, preferably tertiary butyl hypochlorite is contacted with an olefinically unsaturated compound and water, which is essentially free of chloride ion, to produce the chlorohydrin.

The production of chlorohydrin is preferably effected as hereinabove indicated, with water which is essentially free of chloride ion in that it has been found that the presence of chloride ion, in the aqueous phase, reduces the production of the desired chlorohydrin product. The water employed as feed to the chlorohydrinator should not contain a chloride ion concentration in excess of 1 mole/liter, and preferably the chloride ion concentration should not exceed 0.3 mole/liter. The term "essentially free of chloride ions" encompasses a chloride ion concentration of from 0 to 1 mole of chloride ions per liter of water. Furthermore, the presence of chlorine in the chlorohydrin production reactor should be avoided in that such chlorine is converted to the dichloro derivative, rather than the desired chlorohydrin; however, as a result of equilibrium considerations, some dissolved chlorine is introduced with the tertiary alkyl hypochlorite. The amount of free chlorine is maintained as low as possible, and generally does not exceed 7 moles of chlorine per 100 moles of hypochlorite. It is to be understood that greater amounts of chlorine could be present, but such greater amounts reduce the yield of chlorohydrin.

In accordance with a preferred procedure, it has been found that the presence of some salt in the aqueous portion of the chlorohydrin effluent favors extraction of the chlorohydrin and t-alkanol product into the organic phase, thereby facilitating subsequent separation of the effluent into an aqueous phase, for recycle to the chlorohydrin production, and an organic phase, which includes the t-alkanol and chlorohydrin as feed to the saponification. Such salts may include one or more of sodium chloride, sodium sulfate, sodium carbonate, potassium carbonate, calcium chloride, potassium fluoride, etc. Sodium sulfate may be preferred. The salt is employed in concentration which enhances extraction of organics into the organic phase without adversely affecting chlorohydrin production. Thus, if the salt is a chloride, the chloride ion concentration should be below 1 mole per liter of water.

Thus, in a accordance with the present invention, the chlorohydrin effluent is separated into an aqueous phase, which is recycled to the chlorohydrin production reactor, in a manner consistent with the procedure of U.S. Pat. No. 4,008,133, and an organic phase, containing the organic solvent, chlorohydrin and t-alkanol (with only a minimal amount of dissolved water) which may be employed as feed to the saponification. Such organics are therefore recovered without requiring distillation.

The chlorohydrination of the olefin, with the tertiary alkyl hypochlorite, in water, is preferably effected at a temperature from about 70° to about 140° F., and a pressure from 1 psig to about 300 psig. It is to be understood, however, that such conditions are not limiting, and the selection of particular conditions is deemed to be within the scope of those skilled in the art from the teachings herein. The chlorohydrination is preferably effected by concurrent contact in a multistaged stirred reactor, but it is to be understood that cocurrent or counter-current operation or a single stage reactor could be employed.

Organics are extracted from the effluent by the use of an organic extraction solvent, which can be added to the effluent, or in the alternative could be introduced into the chlorohydrin production reactor. In general, such extraction is effected at an elevated temperature in that higher temperatures tend to favor the equilibrium concentration of the tertiary alkanol in the organic extraction solvent. This is particularly true where the aqueous concentration in the effluent is low; i.e., ten weight percent or lower. Thus, for example, such extraction may be effected at temperatures in the order of from about 150° to 200° F. in order to favor the equilibrium concentration of the tertiary alkanol into the organic solvent phase. As previously indicated, the presence of salt in the aqueous phase also favors extraction of organics.

The organic extract is then saponified by direct contact with cell liquor obtained from the cathode compartment of the electrolytic cell, which contains sodium hydroxide and sodium chloride, which reacts with the chlorohydrin to produce the epoxy compound. In general, the saponification is effected at temperatures in the order of from about 150° to about 250° F., preferably from about 180° to about 230° F., at the pressure of the system.

The epoxy compound is recovered from the saponification effluent. In accordance with the present invention, tertiary alkanol present in the saponification effluent is recovered for recycle to the hypochlorite production by extracting the tertiary alkanol into an aqueous phase; in particular either aqueous brine from the saponification and/or an aqueous phase derived from the electrolytic cell and/or aqueous brine from the hypochlorite production.

In accordance with one embodiment, the tertiary alkanol is preferentially extracted into the aqueous brine phase of the saponification effluent. Such preferential extraction may be accomplished by the use of reduced temperatures in that lower temperatures favor the equilibrium concentration of tertiary alkanol into the aqueous brine. Thus, for example, temperatures in the order of 90° F. to 115° F. may be employed.

As hereinabove noted, the presence of salt in the aqueous phase reduces the solubility of tertiary alkanol in the aqueous phase. As a result, in order to increase the tertiary alkanol carrying capacity of the aqueous phase present in the saponification effluent, the volume of such phase may be increased by employing all or portion of the cell liquor to be employed as feed to the hypochlorite production in the organic-aqueous phase separation of the saponification effluent. Thus, the tertiary alkanol is recovered from the saponification effluent in a combined aqueous phase of aqueous brine present in the saponification effluent and cell liquor to be used as feed to the hypochlorite production, with the combined aqueous phase, including tertiary alkanol being introduced into the hypochlorite production step. As hereinabove described, such extraction is favored by lower temperatures.

The volume of such aqueous phase may also be increased by use of a portion of the brine recovered from the hypochlorite production, resulting in the tertiary alkanol being recovered and recycled to the hypochlorite production in a combined aqueous phase comprised of brine produced in the saponification and hypochlorite production. In such an embodiment, there is an internal brine "loop" between the saponification effluent phase separation and the hypochlorite production. As hereinabove described such extraction is favored by lower temperatures.

As a further embodiment, the saponification effluent may be separated into an organic phase and an aqueous brine phase at an elevated temperature whereby the tertiary alkanol is extracted into the organic solvent phase. The aqueous brine phase is ultimately recycled to the electrolytic cell.

The tertiary alkanol is then extracted from the organic solvent into an aqueous phase which is aqueous brine recovered from the hypochlorite production, with the tertiary alkanol being recycled to the hypochlorite production in such aqueous phase. In this manner, there is established an internal brine "loop" between such extraction and the hypochlorite production. Such extraction is effected at the hereinabove noted lower temperatures. In addition, the brine concentration is lower than the brine of the saponification effluent.

The organic solvent present in the saponification effluent is recovered and recycled to the chlorohydrin effluent extraction. As should be apparent, it is not necessary that the organic solvent be free of tertiary alkanol in that such organic solvent is passed in an internal loop between the chlorohydrin effluent extraction and the saponification.

Thus, in accordance with such integrated process the brine produced in the hypochlorite production and saponification steps is ultimately recycled to the cell, and the tertiary alkanol produced in the chlorohydrin production step is recovered in an aqueous phase and recycled to the hypochlorite production.

In accordance with a modified embodiment, the organic phase recovered from the saponification effluent could be contacted with brine free water to "wash" tertiary alkanol therefrom prior to the subsequent extraction step. The tertiary alkanol in such a water extract could then be introduced into the hypochlorite production reactor.

As yet another variation, a portion of the aqueous chlorohydrin production effluent by-passes the extraction step and is fed directly to the saponification reaction. Alternatively, the by-pass portion could be fed directly to a secondary saponification reactor, followed by separation of a crude olefin oxide stream and an aqueous stream containing tertiary alkanol in aqueous brine for introduction into the hypochlorite production reactor.

In accordance with another embodiment, the aqueous raffinate recovered from the extraction step, which is to be recycled to the chlorohydrin production reactor may be treated to separate any residual organic extraction solvent; e.g., the organic extraction solvent may be removed in a stripping operation utilizing live steam or olefin as stripping agent. Such aqueous raffinate may also contain tertiary alkanol, which would be stripped overhead along with the organic solvent. In some cases, final separation of such tertiary alkanol from the organic solvent may be warranted, and this could be accomplished by extracting the tertiary alkanol from the recovered organic extraction solvent with a brine slip stream which is to be introduced into the hypochlorite production reactor.

The olefinically unsaturated compound employed as feed in the present process may be any one of a wide variety of olefinically unsaturated compounds, including both mono-olefinically and diolefinically unsaturated compounds. The olefinically unsaturated compounds generally employed as feed are represented by the following structural formula:

$$R_1-CH=CH-R_2$$

wherein $R_1$ and $R_2$ are each separately either hydrogen; alkyl; halo, naphthyl or phenyl substituted alkyl; halo or alkyl substituted phenyl; phenyl; naphthyl; halo or alkyl substituted naphthyl; alkenyl or halo substituted alkenyl; and $R_1$ and $R_2$ can be linked together to provide a cycloalkene (generally 5 to 10 carbon atoms). The alkyl and alkenyl groups generally contain 1 to 6 carbon atoms and the halo group is preferably iodo-, bromo-, or chloro-, most preferably chloro-. As representative examples of the most suitable feedstocks, there may be mentioned: alkenes having from 2 to 6 carbon atoms, preferably 2 to 4 carbon atoms with ethylene and propylene being particularly preferred; styrene; cyclohexene; stilbene; butadiene; chloroprene; allyl chloride, allyl bromide; bromoprene; cyclohexene, and cyclopentene. The epoxy compounds generally produced in accordance with the invention are represented by the following structural formula:

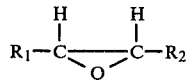

wherein $R_1$ and $R_2$ are as defined above.

Figure 2:
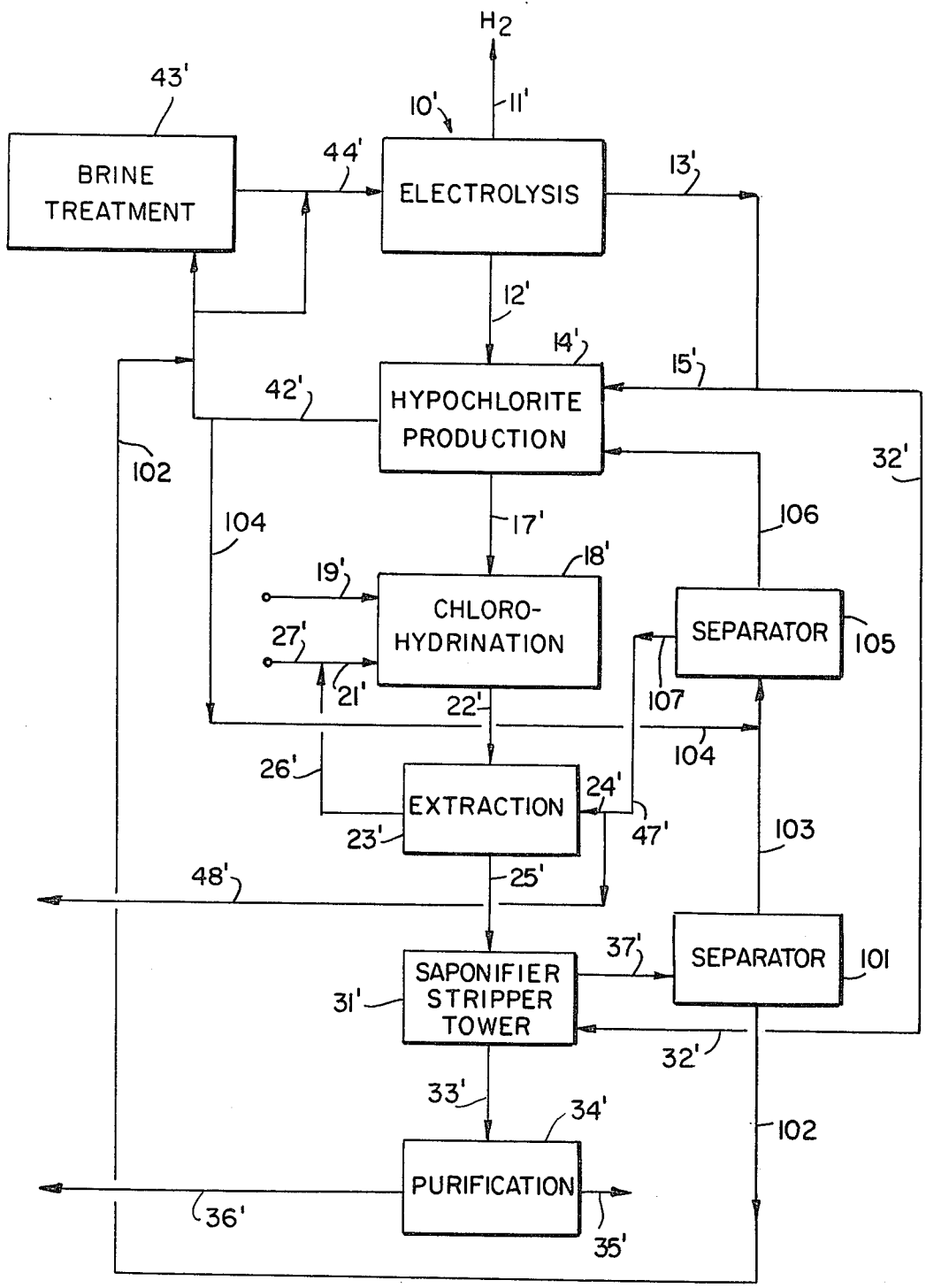

The invention will be further described with respect to a preferred embodiment thereof, illustrated in the accompanying drawing wherein:

FIG. 1 is a simplified schematic flow diagram of an embodiment of the process of the present invention; and FIG. 2 is a simplified flow diagram of another embodiment.

The preferred embodiment will be particularly described with respect to the production of propylene oxide (1, 2-epoxy propane), but it is to be understood that the embodiment is also applicable to the production of other epoxy compounds; e.g., epichlorohydrin from allyl chloride.

Referring to the drawing, there is shown an electrolytic cell, schematically generally indicated as 10, wherein, as known in the art, hydrogen is produced at the cathode, and chlorine at the anode, using sodium chloride as electrolyte. The hydrogen is withdrawn from the cell, as net product, through line 11. Chlorine produced in the cell is withdrawn therefrom through line 12, and caustic cell liquor, containing sodium hydroxide and sodium chloride, dissolved in water, is withdrawn from the cell through line 13.

The chlorine in line 12 is introduced into a hypochlorite production reactor, schematically indicated as 14 wherein the chlorine contacts a tertiary alkanol; in particular, tertiary butanol and caustic cell liquor to effect production of tertiary alkyl hypochlorite. The caustic cell liquor, containing sodium chloride and sodium hydroxide, may be provided directly from the cell through line 15 or may be provided in a recycle brine stream, containing tertiary butanol, as hereinafter described. The tertiary butanol is provided through line 16 in a recycle aqueous brine stream, which may or may not be supplemented with caustic cell liquor, as hereinafter described.

The hypochlorite production reactor 14 is operated as hereinabove described to effect chlorination of the tertiary butanol to tertiary butyl-hypochlorite, which is recovered as an organic stream through line 17.

The production of the hypochlorite and the recovery of the hypochlorite may be effected as described in U.S. Pat. No. 4,008,133, which is hereby incorporated by reference.

The hypochlorite in line 17 is introduced into a chlorohydrin production reaction zone, schematically generally indicated as 18. Propylene, in line 19, as well as a recycle aqueous stream in line 21 are also introduced into the chlorohydrin production reaction zone 18. The chlorohydrin production reaction zone 18 is operated at conditions as hereinabove described to effect conversion of the propylene to propylene chlorohydrin. The chlorohydrin production reactor 18, generally includes means for mixing of the three phases present in the reactor; namely, a gaseous phase, as well as organic and aqueous phase, and such chlorohydrin production may be effected as described in U.S. Pat. No. 4,008,133. It is to be understood that in some cases a catalyst may be introduced into the chlorohydrin production zone in order to increase chlorohydrin production rate.

A liquid reaction effluent, which contains water, tertiary butanol, propylene chlorohydrin, as well as any reaction by-products, is withdrawn from the propylene chlorohydrin production reactor 18 through line 22 and introduced into an extraction column, schematically indicated as 23, wherein the effluent is contacted with an organic extraction solvent introduced through line 24. In particular, the organic extraction solvent could be, for example, dichloropropane, carbon tetrachloride or mixtures thereof. As a result of such contact, organics present in the chlorohydrin production reaction effluent are extracted into the organic solvent phase (propylene chlorohydrin, tertiary butanol, as well as reaction by-products) which is withdrawn from the extraction column 23 through line 25.

An aqueous raffinate is withdrawn from extraction column 23 through line 26, and as hereinabove noted, such aqueous raffinate may include some organic solvent, as well as residual tertiary butanol. If required, as hereinabove described, such organics may be removed in a separate operation, from such aqueous raffinate. The aqueous raffinate in line 26, with or without treatment to remove organics, is combined with makeup water in line 27, and introduced through line 21 into the propylene chlorohydrin production reactor 18.

The organic extract in line 25 is introduced into a saponification reaction zone, which is preferably in the form of a combination saponifier-stripping tower, which is schematically generally indicated as 31. In the saponification reaction zone 31, the organic extract is contacted with caustic cell liquor containing sodium hydroxide, sodium chloride and water, obtained from the electrolysis cell 10, and introduced into the saponification reactor 31 through line 32. As a result of such contact, the propylene chlorohydrin is converted to propylene oxide, and the hydrogen chloride released is neutralized by the sodium hydroxide present in the cell liquor to produce sodium chloride and water.

Crude propylene oxide, which may contain light end products, such as, acetone, is withdrawn from the saponification reactor-stripping tower 31 through line 33 for introduction into a propylene oxide purification section, schematically generally indicated as 34, wherein light end impurities are separated from the propylene oxide. Propylene oxide is recovered as product through line 35, with the light end impurities being recovered through line 36.

Referring back to saponifier-stripping tower 31, a bottoms, containing water, sodium chloride, tertiary butanol, organic solvent, as well as heavier by-products, is withdrawn from the stripping portion of the saponifier through line 37 and introduced into a separator, schematically generally indicated as 38 in order to effect separation of organic and aqueous phases. In accordance with one embodiment, separator 38 is further provided with caustic cell liquor from the electrolysis cell 10 through line 39 in order to increase the ability of the aqueous brine phase to carry tertiary butanol. In accordance with another embodiment, separator 38 may be provided through line 45 with brine recovered from the hypochlorite production to increase the alkanol carrying capacity of the aqueous phase by increasing the bulk volume thereof. It is to be understood, however, that in some cases the separation can be conducted without the addition of additional aqueous material. The separation in separator 38 is effected in a manner such that the equilibrium concentration of tertiary butanol is in favor of the aqueous brine phase.

An aqueous brine phase, which contains tertiary butanol, and which may further contain sodium hydroxide, if cell liquor is provided through line 39, is withdrawn from separator 38 through line 16 for introduction into the hypochlorite production reactor 14. Make up tertiary butanol, if required, may be provided through line 41. All or a portion of the caustic requirements, or none of the caustic requirements for the hypochlorite production reactor 14 may be provided through line 16, depending on whether or not cell liquor is provided to separator 38 through line 39. The remaining portion of the caustic requirements, if any, are provided by the introduction of cell liquor through line 15.

An aqueous brine phase is withdrawn from the hypochlorite production reactor 14 through line 42 for recycle to the electrolytic cell 10. A portion of the brine solution may be passed through line 45 to separator 38, as hereinabove described. All or a portion of the remaining brine solution may be directly recycled to electrolytic cell 10; however, in accordance with a preferred embodiment, at least a portion of such recycle brine solution is introduced into a brine purification section, schematically generally indicated as 43 in order to remove organic contaminants therefrom. Such purification may be effected as described in U.S. Application Ser. No. 851,853, filed on Nov. 16, 1977, which is hereby incorporated by reference. The recycled brine solution is introduced into the electrolytic cell 10 through line 44.

Referring back to separator 38, an organic phase, containing the extraction solvent, as well as some tertiary butanol and heavier by-products, is withdrawn from separator 38 through line 47 for recycle to the extraction column 23 through line 24. A slip-stream of such organic phase may be withdrawn through line 48 for introduction with light impurities in line 36 into an incinerator, along with molecular oxygen, as described in U.S. Pat. No. 4,008,133.

Alternatively, all or a portion of such organic by-products may be separately recovered. As a further alternative, the extraction solvent may be water "washed" in order to remove tertiary butanol therefrom, which such tertiary butanol being ultimately introduced into the hypochlorite production reactor 14.

A further embodiment of the invention is shown in FIG. 2 of the drawings. The embodiment of FIG. 2 is similar to the embodiment of FIG. 1, except for the recovery of tertiary alkanol from the saponification effluent for recycle to the hypochlorite production. As a result, the embodiment of FIG. 2 will be particularly described only with respect to such recovery portion. In FIG. 2, prime numerals are employed to designate the portions of the embodiment similar to the embodiment of FIG. 1.

Referring to FIG. 2, a bottoms containing water, sodium chloride, tertiary butanol, organic solvent, as well as heavier byproducts, is withdrawn from the stripping portion of the saponifier through line 37' and introduced into a separator 101 to separate organic and aqueous phases. The separation in separator 101 is conducted at conditions such that essentially all of the tertiary butanol is extracted into the organic phase; i.e., higher temperatures and higher salt concentrations.

Aqueous brine is withdrawn from separator 101 through line 102 and may be combined with net brine from the hypochlorite production for recycle to the electrolysis.

An organic phase containing the tertiary butanol withdrawn from separator 101 through line 103 is combined with the brine in line 45' recovered from the hypochlorite production and the combined stream introduced into a second separator 105. The separator 105 is operated at conditions which favor extraction of the tertiary butanol into the aqueous phase; i.e. lower temperatures and lower salt concentrations.

Aqueous brine, containing tertiary butanol is withdrawn from separator 105 through line 106 and recycled to the hypochlorite production.

Organic solvent is recovered from separator 105 through line 47' for recycle to the chlorohydrin effluent extraction.

In accordance with this embodiment, it is possible to effect t-butanol recovery while maintaining a higher salt concentration in the brine recycle from the saponification. Such higher salt concentration is advantageous in the operation of the electrolytic cell. Thus, for example, whereas the saponification effluent brine should have a relatively low salt concentration (17–18 wt%) to provide for economic extraction directly into the aqueous phase, by proceeding in accordance with the embodiment of FIG. 2 it is possible to employ higher salt concentrations; e.g., about 25 wt%, whereby the concentration of total brine recycled to the cell is increased.

Although the invention has been described with respect to preferred embodiments, it is to be understood that such embodiments may be varied in numerous ways within the spirit and scope of the present invention. As a result, the present invention is not limited to such embodiments.

For example, as hereinabove noted, the invention is also applicable to the production of epoxy compounds by use of hypochlorite, without integration with electrolytic production of chlorine. Thus, the chlorine and/or the aqueous base employed in the hypochlorite production and/or saponification may be obtained from other sources. Thus, the present invention is generally applicable to the production of epoxy compounds by use of hypochlorite wherein organics are recovered from the chlorohydrin production effluent in an organic solvent which is employed as feed to the saponification, with tertiary alkanol being ultimately recovered from the saponification effluent in an aqueous phase which is recycled to the hypochlorite production.

The present invention is further illustrated by the following example; however, the scope of the invention is not to be limited thereby:

EXAMPLE

The following presents in tabular form the temperatures, compositions and flow rates of various streams of the embodiment illustrated in the drawing (FIG. 1) with respect to the use of an organic extraction solvent for effecting recovery of chlorohydrin and tertiary alkanol.

| Stream No. | Temp. Range (°F.) | Principal Component Concentration Ranges (Weight %) | Total Flow Range (M Lb/Hr.) |
|---|---|---|---|
| | | BASIS: 100 MM Lb/Yr. Propylene Oxide Production Capacity | |
| 24 | 150–200 | 5–15% t-BuOH (t-Butanol) Bal. DCP (Dichloropropane), etc. | 50–200 |
| 22 | 115–140 | 5–15% t-BuOH 5–19% $C_3H_7OCl$ Bal. $H_2O$ | 100–400 |
| 25 | 125–175 | 10–25% t-BuOH 10–25% $C_3H_7OCl$ Bal. DCP/etc. | 100–250 |
| 32 | 175–200 | 7–12% NaOH 7–15% NaCl Bal. $H_2O$ | 75–150 |
| 26 | 150–175 | 1–7% t-BuOH 0–5% $C_3H_7OCl$ Bal. $H_2O$ | 75–200 |
| 33 | 150–200 | 50–99% P.O. Bal. $H_2O$ | 12–25 |
| 37 | 175–250 | | 150–400 |
| 39 | 90–125 | 7–12% 7–15% NaCl Bal. $H_2O$ | 0–150 |
| 16 | 90–125 | 0–6% NaOH 2–7% t-BuOH 15–25% NaCl Bal. $H_2O$ | 200–900 |
| 45 | 90–125 | 15–25% NaCl Bal. $H_2O$ | 100–800 |

The present invention is particularly advantageous in that it permits effective production of an olefin oxide, while facilitating recovery of various components produced in the process. In particular, the present invention provides for recovery of chlorohydrin and recycle alkanol without the necessity of employing costly azeotropic distillation procedures.

The above advantages and others should be apparent to those skilled in the art from the teachings herein.

Numerous modifications and variations of the present invention are possible in light of the above teachings and, therefore, within the scope of the appended claims, the invention may be practised otherwise than as particularly described.

What is claimed:

1. In a process for producing an epoxy compound which is integrated with the electrolytic production of chlorine wherein a tertiary alkanol is contacted with chlorine and aqueous electrolyte from the electrolytic cell, containing sodium hydroxide and sodium chloride to produce tertiary alkyl hypochlorite and aqueous brine for ultimate recycle to the cell, tertiary alkyl hypochlorite is contacted with olefinically unsaturated compound and water to produce the corresponding chlorohydrin and tertiary alkanol, and chlorohydrin is contacted with aqueous electrolyte from the electrolytic cell containing sodium chloride and sodium hydroxide to produce the corresponding epoxy compound and aqueous brine for ultimate recycle to the cell, the improvement comprising:
   extracting organics from the chlorohydrin production with an organic extraction solvent to produce an organic extract containing chlorohydrin and tertiary alkanol; contacting organic extract with the aqueous electrolyte containing sodium chloride and sodium hydroxide to saponify chlorohydrin to the corresponding epoxy compound;
   recovering epoxy compound;
   separating from the saponification an organic solvent phase and an aqueous phase, said separation being effected with preferential extraction of the tertiary alkanol into the organic solvent phase;
   extracting tertiary alkanol from the organic solvent phase with an aqueous phase derived from the hypochlorite production;
   passing said aqueous phase derived from the hypochlorite production containing extracted tertiary alkanol to said hypochlorite production; and
   recycling organic solvent to said extracting of organics.

2. The process of claim 1 wherein the organic extraction solvent is comprised of at least one chlorinated hydrocarbon.

3. The process of claim 2 wherein the tertiary alkanol is tertiary butanol.

4. The process of claim 3 wherein the extraction into the aqueous phase is at a temperature of from 90° F. to 115° F.

5. The process of claim 3 wherein the olefinically unsaturated compound is propylene.

6. The process of claim 3 wherein the olefinically unsaturated compound is allyl chloride.

7. In a process for producing an epoxy compound wherein a tertiary alkanol is chlorinated in the presence of an aqueous base to produce tertiary alkyl hypochlorite, the tertiary alkyl hypochlorite is contacted with an olefinically unsaturated compound and water to produce a reaction effluent containing water, tertiary alkanol and chlorohydrin, and the chlorohydrin is saponified with aqueous base to produce the corresponding epoxy compound, the improvement comprising:
   extracting organics from the chlorohydrin production with an organic extraction solvent, said organics including the chlorohydrin and tertiary alkanol;
   contacting organic extract containing chlorohydrin and tertiary alkanol, and an aqueous base to effect saponification of the chlorohydrin to the corresponding epoxy compound;
   recovering the epoxy compound produced in the saponification;
   separating from the saponification an organic solvent phase and an aqueous brine phase, said separating being effected with preferential extraction of the tertiary alkanol into the organic solvent phase;
   extracting tertiary alkanol from the organic solvent phase with aqueous brine derived from the hypochlorite production;
   passing aqueous brine containing extracted tertiary alkanol to the hypochlorite production; and
   recycling organic solvent to said extracting of organics.

8. The process of claim 7 wherein a water phase is recovered from the chlorohydrin production and recycled to the chlorohydrin production.

9. The process of claim 8 wherein the water employed in the chlorohydrin production has a salt dissolved therein to enhance extraction of the tertiary alkanol and chlorohydrin into the inert organic solvent.

10. The process of claim 7 wherein the tertiary alkanol is tertiary butanol.

11. The process of claim 10 wherein the extraction into the aqueous phase is at a temperature of from 90° F. to 115° F.

12. The process of claim 10 wherein the olefinically unsaturated compound is propylene.

13. The process of claim 10 wherein the olefinically unsaturated compound is allyl chloride.

* * * * *